United States Patent
Odén

(10) Patent No.: US 10,137,065 B2
(45) Date of Patent: Nov. 27, 2018

(54) DEODORANT COMPOSITION AND DEODORANT PRODUCT COMPRISING A DEODORANT COMPOSITION

(71) Applicant: ODOURLESS SWEDEN AB, Malmö (SE)

(72) Inventor: Thomas Odén, Ljungsbro (SE)

(73) Assignee: ODOURLESS SWEDEN AB, Malmö (SE)

(*) Notice: Subject to any disclaimer, the term of this patent is extended or adjusted under 35 U.S.C. 154(b) by 0 days.

(21) Appl. No.: 15/567,727

(22) PCT Filed: Mar. 20, 2016

(86) PCT No.: PCT/SE2016/050235
§ 371 (c)(1),
(2) Date: Oct. 19, 2017

(87) PCT Pub. No.: WO2016/171600
PCT Pub. Date: Oct. 27, 2016

(65) Prior Publication Data
US 2018/0116919 A1     May 3, 2018

(30) Foreign Application Priority Data
Apr. 23, 2015 (SE) ...................... 1550485

(51) Int. Cl.
| | |
|---|---|
| *A61K 8/02* | (2006.01) |
| *A61K 8/04* | (2006.01) |
| *A61K 8/19* | (2006.01) |
| *A61K 8/23* | (2006.01) |
| *A61Q 15/00* | (2006.01) |

(52) U.S. Cl.
CPC ............. *A61K 8/19* (2013.01); *A61K 8/0208* (2013.01); *A61K 8/046* (2013.01); *A61K 8/23* (2013.01); *A61Q 15/00* (2013.01); *A61K 2800/30* (2013.01); *A61K 2800/48* (2013.01); *A61K 2800/524* (2013.01)

(58) Field of Classification Search
CPC ............ A61K 2800/30; A61K 2800/48; A61K 2800/524; A61K 8/0208; A61K 8/046; A61K 8/19; A61K 8/23; A61Q 15/00
See application file for complete search history.

(56) References Cited

U.S. PATENT DOCUMENTS

| | | | |
|---|---|---|---|
| 4,879,105 A * | 11/1989 | Yorozu | A61K 8/19 424/44 |
| 5,411,731 A | 5/1995 | Tanaka et al. | |
| 6,440,415 B1 | 8/2002 | Johnson | |
| 2008/0241200 A1* | 10/2008 | Sojka | A61K 8/0208 424/401 |
| 2009/0214628 A1* | 8/2009 | de Rijk | A01N 59/00 424/450 |

FOREIGN PATENT DOCUMENTS

| | | |
|---|---|---|
| CN | 1353997 A | 6/2002 |
| CN | 103190412 A | 7/2013 |

OTHER PUBLICATIONS

Doyle, C. "Spray deodorant", No Trash Project, 2012, retrieved Oct. 1, 2015. URL: http://notrashproject.com/tag/natural-deodorant/> (6 pages).
International Search Report and Written Opinion for International Application No. PCT/SE2016/050235 dated May 4, 2016 (13 pages).
Lamb, J. "Sodium Bicarbonate: An Excellent Deodorant" The Journal of Investigative Dermatology 7 (1946) pp. 131-133 (4 pages).
Mintel, "Baking Soda Roll-on Deodorant", GNPD, Jul. 1, 2010, Retrieved from EPODOC (2 pages).
Mintel, "Fragrance Free Aluminum Free Deodorant", GNPD, Nov. 1, 2006, Retrieved from EPODOC (2 pages).

* cited by examiner

*Primary Examiner* — Michael B. Pallay
(74) *Attorney, Agent, or Firm* — RMCK Law Group, PLC

(57) ABSTRACT

The present invention relates to a cosmetic composition which is an antiperspirant and/or deodorant fluid composition to be applied to the human skin, the composition being a non-aluminum based fluid composition free from alcohols and oils, comprising sodium or potassium bicarbonate as the essential deodorizing agent.

10 Claims, 3 Drawing Sheets

DEODORANT COMPOSITION AND DEODORANT PRODUCT COMPRISING A DEODORANT COMPOSITION

CROSS-REFERENCE TO RELATED APPLICATIONS

This application is a 371 U.S. National Stage of International Application No. PCT/SE2016/050235, filed Mar. 22, 2016, which claims priority to Swedish Application No. 1550485-5, filed on Apr. 23, 2015. The disclosures of each of the above applications are incorporated herein by reference in their entirety.

TECHNICAL FIELD

The present invention relates to a fluid deodorant composition which has excellent deodorizing effects on the odors of armpits, foot and the body of humans, etc. to give comfort after use.

BACKGROUND OF THE INVENTION

Antiperspirants combat axillary odors by inhibiting perspiration through the action of astringent salts such as aluminum and zinc salts. Deodorants function by neutralizing the objectionable odors resulting from the degradation of several components of perspiration by chemical and microbial action into malodorous fatty acids.

Unfortunately, the mentioned aluminum salts have been the subject of as-yet unresolved concerns about their long-term health effects. Some people are allergic to aluminum and may suffer contact dermatitis after using aluminum-containing antiperspirants. Some reports have linked aluminum-containing antiperspirants with the systemic accumulation of aluminum in the body.

Efforts to provide aluminum-free deodorants for underarm use include products with synthetic antibacterial agents such as Triclosan, which at high levels have prompted concerns by some groups. Bacterial inhibition has also been attempted with botanical ingredients such as Phellodendron Amurense Bark Extract which is said to help inhibit sweat-induced odor. However, both synthetic and bio-derived ingredients previously used for this purpose may cause irritation of the skin or may not provide other beneficial properties with respect to skin and hair in the region of application.

Given the limitations in currently available products, there is a need for deodorants and antiperspirants that are effective in preventing perspiration or associated odor on the body, while reducing perceived health risks associated with aluminum compounds or other harsh chemicals.

SUMMARY OF THE INVENTION

In view of above-mentioned and other drawbacks of the prior art, it is an object of the present invention to provide an improved composition providing adequate deodorizing/antiperspirant effect with a reduced risk for health related issues.

According to an aspect of the present invention, it is therefore provided a cosmetic composition which is an antiperspirant and/or deodorant composition to be applied to the human skin, the composition being a non-aluminum based composition free from oils and alcohols as an antiseptic, wherein the composition comprises from about 3.0 to about 5.0 weight percent of an alkali metal bicarbonate, from about 0.1 to about 1.0 weight percent of sodium carbonate, and from about 0.1 to about 3.0 weight percent of sodium sulphate, wherein the alkali metal bicarbonate, sodium carbonate and the sodium sulphate are dissolved in water.

As used herein, "deodorants" and "antiperspirants" both refer to compositions that are effective in directly or indirectly reducing unwanted body odors associated with perspiration and/or bacteria on the surface of the skin. "Deodorants" may reduce odor through a variety of means, and such means in the various embodiments of the present invention may include suppression of bacterial activity, antimicrobial mechanisms, chemical interference with odor generation mechanisms, removal or modification of feedstuff for odor-producing bacteria, and the like. "Antiperspirants" generally work to reduce the production of perspiration. A deodorant may function as an antiperspirant but need not do so to be a deodorant. The compositions of various embodiments of the present invention may generally be described as deodorants and in many cases may generally be described as antiperspirants, though a composition that has limited antiperspirant efficacy is not necessarily outside the scope of the present invention.

The present invention is based upon the realization that the disclosed composition, and specifically when selected to be combined in a manner as mentioned above, will have an improved deodorizing/antiperspirant effect as compared to e.g. prior art aluminum based deodorizing composition. In addition, no "clogging" of the pores of the skin is provided, as is the case with aluminum based compositions for retarding or inhibiting the flow of perspiration.

Within the water based composition, the alkali metal bicarbonate acts as the main deodorizing agent. The addition of the sodium carbonate to the composition further increases the deodorizing/antiperspirant effect. Solely using sodium carbonate would however not be suitable for application to the human skin. Furthermore, sodium sulphate is in accordance to the invention at least partly used for moisturizing the skin. Hence, the amount of sodium sulphate selected for use in the deodorizing component according to the invention thus allows for an optimal deodorizing effect while at the same time keeping the risk for a skin reaction to a minimum.

The chemical explanation of why bicarbonate of soda should act as a deodorant is of interest. Sweat has an acid reaction, pH of 5.2-6.75 which is due to the fatty acids or acid phosphates of sodium and potassium which it contains. It also contains NaCl, KCl, alkaline salts, organic acids and urea. Minute amounts of unstable fats and oils are secreted in sweat and hydrolysed to their corresponding fatty acids and glycerin. Free fatty acids may be secreted. Many of these acids are volatile and have a characteristic disagreeable odor. These include butyric acid, formic acid, caproic acid and valeric acid. The following are among the possible explanations of the manner in which sodium bicarbonate acts as a deodorant in e.g. the axilla. It forms a sodium salt with butyric, caproic and valeric acids. These sodium salts are comparatively mild in odor in comparison to the volatile "rancid-smelling" fatty acids.

In a preferred embodiment, the composition comprises from about 4.0 to about 4.8 weight percent of the alkali metal bicarbonate, from about 0.3 to about 0.5 weight percent of sodium carbonate, and from about 0.4 to about 0.8 weight percent of sodium sulphate. The inventor has shown that this composition has a surprisingly positive effect on reducing the odor and preventing perspiration of the human body. In addition, the proposed composition has still a limited risk of affecting the human body in a negative manner, i.e. in regards to skin reactions.

It is desirable to select the alkali metal bicarbonate to be sodium bicarbonate or potassium bicarbonate or a mixture thereof. It may in some instances be most preferred to use sodium bicarbonate.

In a possible embodiment of the invention, the composition further comprises at least one of a preservative and a thickener. The selection of preservative is highly relevant for use in relation to the human body. Accordingly, in one embodiment the composition comprises a preservative and/or a thickener. As the inventive composition has a relatively high pH level, the common types of preservatives are not suitable components for the composition. In a specific embodiment of the invention a preservative being active within the range at and/or above pH 8.0 is selected. In addition, it is preferred to select a preservative not comprising paraben. It should further be understood that definition according to the invention that the composition is free from alcohols as an antiseptic does not include possible alcohol derivatives used in preservatives, such as e.g. Phenoxyethanol, solely used against e.g. bacteria and yeasts. As mentioned, it may also be possible to include a thickener with the composition. However, the use of a thickener may be allowed to depend on how the composition is applied and/or distributed on the human body.

As such, in an embodiment there is provided a cosmetic deodorant product, comprising the composition as discussed above and a carrier for holding the composition. In one embodiment the carrier may be a spray dispensing container, pressurized or using a pump functionality.

In another embodiment the carrier is selected to be a towelette. The towelette may in such an embodiment be arranged in a sealed container for enclosing the towelette, where a volume of fluid composition is located within the container, and the towelette is immersed in the volume of fluid composition located within the container and would absorb some or all of the volume of fluid composition located within the container.

In still another embodiment the carrier is a fluid applicator, such as for example a roll-on container. Depending on the type of roll-on container it may be desirable to arrange the composition to also include the above mentioned thickener. However, in a specific embodiment of the invention the fluid applicator is a Dab-O-Matic fluid container. The Dab-O-Matic fluid container removes the necessity of using a thickener with the composition. The Dab-O-Matic fluid container is based on the use of a textile portion arranged under a sealing cap. When applying a (small) pressure to the textile portion, a (small) volume of the composition is release, to be wiped against the skin. The removal of the necessity of using a thickener may in some instances be advantageous, and some thickeners may be skin irritant some persons.

It should be understood that any suitable carrier may be used to dispense the inventive composition onto the skin. The composition according to the present invention may be provided in any suitable form such as a e.g. a viscous hydrogel, a substantially solid gel, a spray (using an aerosol or pump), a lotion, a powder, a suspension, a wipe, a foam, etc. Delivery of active ingredients can be via any known method such as by spraying, wiping, extruding, pouring, rinsing, application with the fingers, etc., and combinations thereof.

According to a further aspect of the present invention, there is provided a method for deodorizing a malodor, which comprises applying the composition as discussed above.

This aspect of the invention provides similar advantages as discussed above in relation to the previous aspect of the invention.

According to a still further aspect of the invention there is provided the use of the composition as discussed above for deodorizing a malodor. Also this aspect of the invention provides similar advantages as discussed above in relation to the previous aspects of the invention.

In summary, present invention generally relates to a cosmetic composition which is an antiperspirant and/or deodorant composition to be applied to the human skin, the composition being a non-aluminum based composition free from alcohols and oils, comprising sodium or potassium bicarbonate as the essential deodorizing agent.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1:
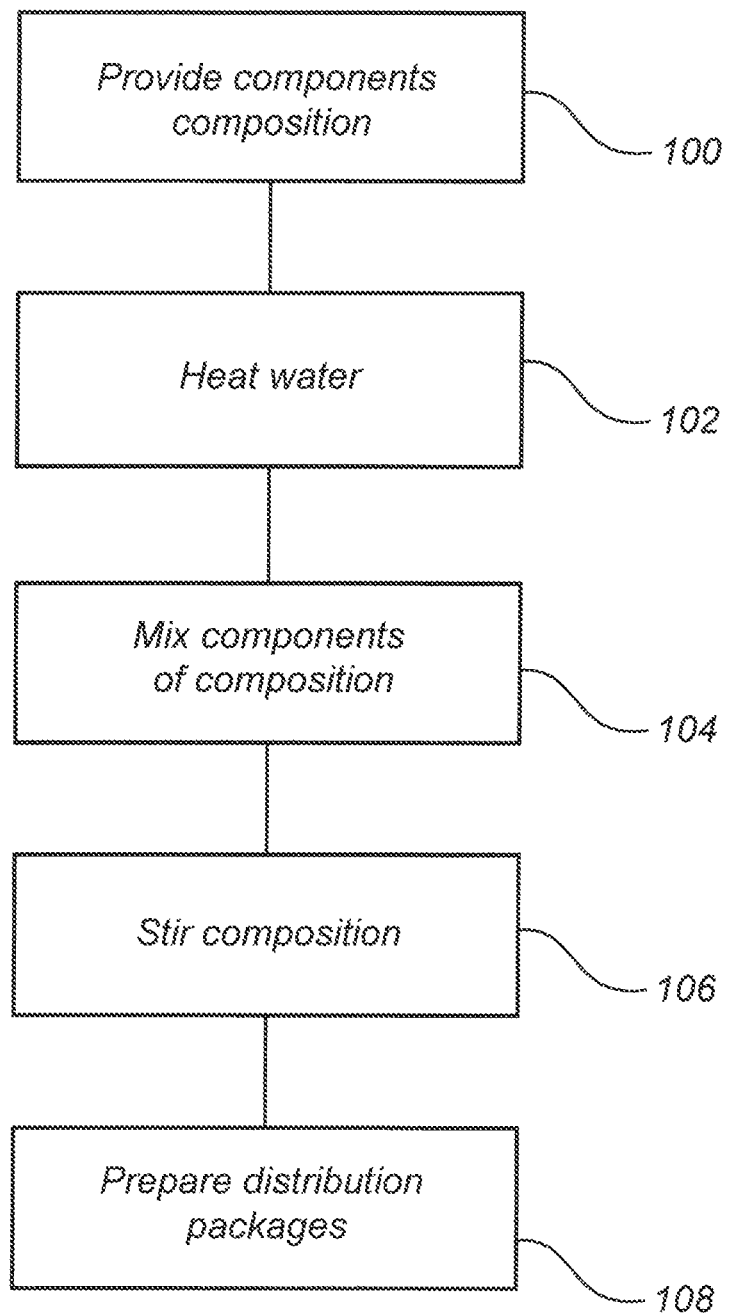
FIG. 1 is a flowchart illustrating the steps of preparing the fluid cosmetic composition according to the invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person. Like reference characters refer to like elements throughout.

Turning now to the drawings and to FIG. 1 in particular, there is flowchart illustrating the steps of preparing the fluid cosmetic composition according to the invention. In an exemplary non-limiting preparation of the inventive fluid cosmetic composition, a volume of 1000 liters of water is provided, 100, together with 45 kg of sodium bicarbonate, 4 kg of sodium carbonate and 6 kg of sodium sulphate. The water is heated, 102, and the "dry components" (i.e. sodium bicarbonate, sodium carbonate and sodium sulphate) of the composition are mixed/dissolved, 104, in the water by stirring 106. It is desirable to allow all content of the dry components to be completely dissolved with the water.

It is desirable to at this stage control the pH level and then introduce the above discussed preservative, being selected specifically to be active within a pH range comprising pH 8.0. It may also, optionally, be possible to introduce a thickener, depending on the selection of distribution package for the fluid cosmetic composition.

In a final step, following a cooling down period for the inventive fluid cosmetic composition, the fluid cosmetic composition is prepared, 108, in selected packaging container as will be further discussed below in relation to FIGS. 2-4.

Figure 2:
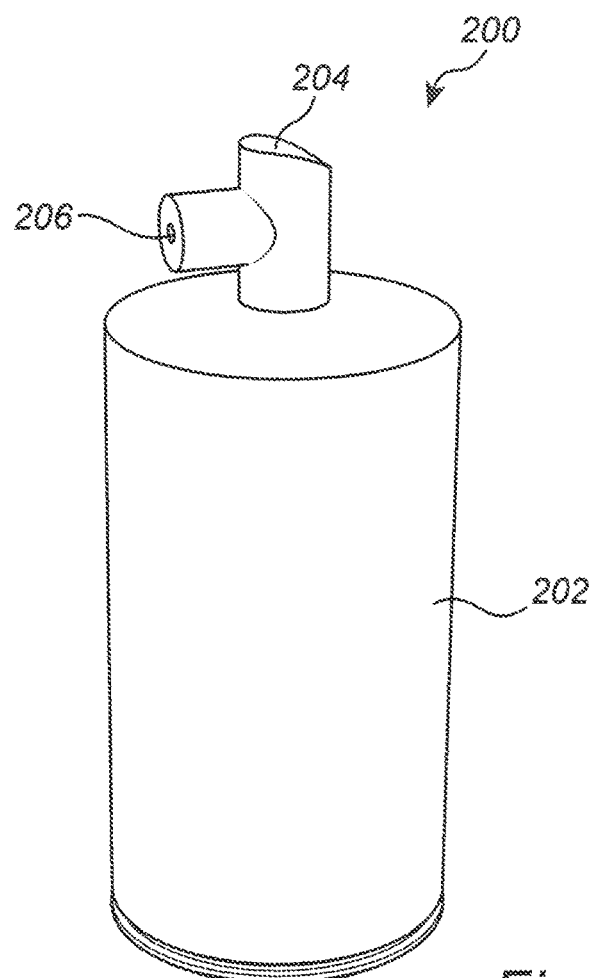
FIG. 2 illustrates an aerosol dispensing arrangement comprising a cosmetic composition according to certain embodiments of the present invention.

FIG. 2 illustrates an exemplary aerosol dispensing arrangement 200 for holding the inventive composition to be applied to the human skin. The aerosol dispensing arrangement 200 comprises a container 202, for example made of plastic. Other suitable materials may also be selected, such as metal. In the illustrated embodiment, the container 202 is shown having the form of a cylinder, comprising a dispending cap 204. The container 200 may use pump functionality for extracting the composition from the container, or may in another embodiment use a propellant. The propellant may for example be a liquefied normally-gaseous medium preferably selected from the group consisting of hydrocarbons and halogenated hydrocarbons and mixtures thereof. During use, the dispending cap 204 is activated and a nozzle 206 will form an aerosol of the composition, where the aerosol is allowed to contact the human skin.

Figure 3:
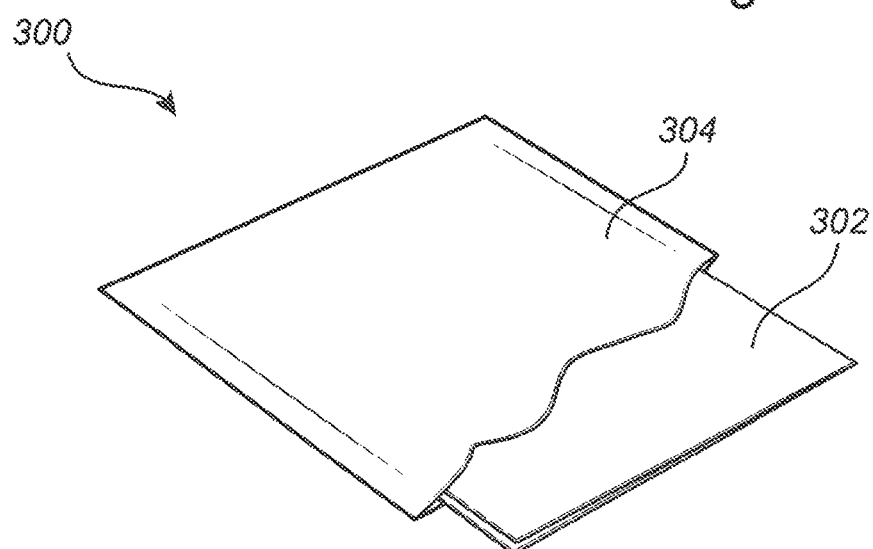
FIG. 3 depict a towelette arranged in a sealed container according to a certain embodiment of the present invention.

In FIG. 3 there is illustrated a deodorant towelette arrangement 300 comprising a folded towelette 302 to, before use, being arranged inside of a package 304. The package 404 may in some embodiment comprise an aluminum foil, but may also be made from plastic and/or paper. The towelette 302 would be immersed in the inventive composition. Due to the sealed package 304, the deodorant towelette arrangement 300 would be capable of being stored for long periods of time until needed for use. When used, the sealed package 304 is broken, the towelette 302 typically unfolded and wiped at the human skin.

Figure 4:
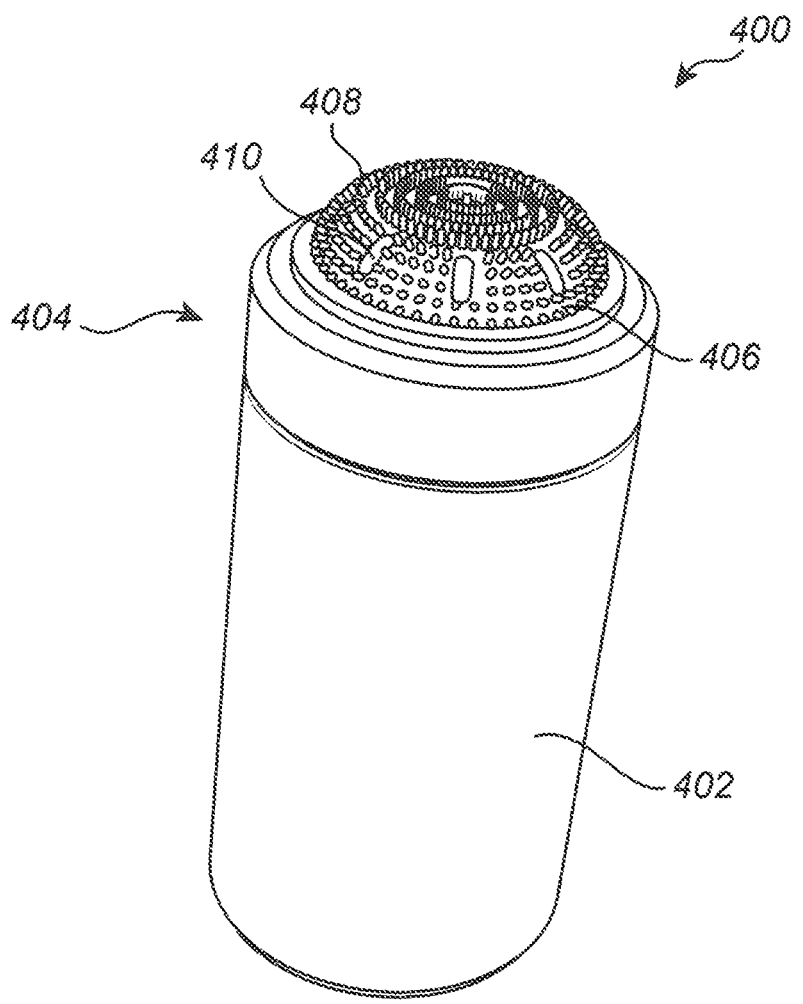
FIG. 4 illustrates a fluid applicator for holding the composition according to a currently preferred embodiment of the present invention.

FIG. 4 illustrates a fluid applicator 400 for holding the inventive composition for application to the human skin. The fluid applicator 400 comprises a container 402 and a distribution cap 404. The distribution cap 404 is fitted to the container 402, and during non-use of the fluid application 400, distribution cap 404 provides a seal against unwanted fluid discharge of the fluid composition according to the invention.

The distribution cap 404 comprises a flexible diaphragm 406 provided with a plurality of protrusions 408 and slots 410. Pressure on the diaphragm 406 and/or the protrusions 408 opens a fluid passage so that the fluid composition according to the invention can pass from the container 402 and through the slots 410 for application to the human skin.

When introducing elements of aspects of the invention or the embodiments thereof, the articles "a," "an," "the," and "said" are intended to mean that there are one or more of the elements, and thus may include plural referents unless the context clearly dictates otherwise. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above compositions, products, and methods without departing from the scope of aspects of the invention, it is intended that all matter contained in the above description shall be interpreted as illustrative and not in a limiting sense.

In addition, variations to the disclosed embodiments can be understood and effected by the skilled addressee in practicing the claimed invention, from a study of the drawings, the disclosure, and the appended claims.

The invention claimed is:

1. A fluid cosmetic composition which is an antiperspirant and/or deodorant composition to be applied to the human skin, the composition being a non-aluminum based composition free from oils and alcohols as an antiseptic, wherein the composition comprises:
   from 3.0 to 5.0 weight percent of an alkali metal bicarbonate;
   from 0.1 to 1.0 weight percent of sodium carbonate, and
   from 0.1 to 3.0 weight percent of sodium sulphate, wherein the alkali metal bicarbonate, sodium carbonate and the sodium sulphate are dissolved in water.

2. The fluid composition according to claim 1, wherein the composition comprises:
   from 4.0 to4.8 weight percent of the alkali metal bicarbonate;
   from 0.3 to 0.5 weight percent of sodium carbonate, and
   from 0.4 to 0.8 weight percent of sodium sulphate.

3. The fluid composition according to claim 1, wherein the alkali metal bicarbonate is sodium bicarbonate or potassium bicarbonate or a mixture thereof.

4. The fluid composition according to claim 1, wherein the composition further comprises at least one of a preservative and a thickener.

5. A cosmetic deodorant product, comprising:
   the fluid composition according to claim 1, and
   a carrier for holding the fluid composition.

6. The deodorant product according to claim 5, wherein the carrier is a spray dispensing container.

7. The deodorant product according to claim 5, wherein the carrier is a towelette.

8. The deodorant product according to claim 7, wherein:
   the towelette is arranged in a sealed container for enclosing the towelette;
   a volume of the fluid composition located within the container, and
   the towelette being immersed in the volume of fluid composition located within the container and configured to absorb some or all of the volume of the fluid composition located within the container.

9. The deodorant product according to claim 5, wherein the carrier is a fluid applicator.

10. A method for deodorizing a malodor, which comprises applying the fluid composition according to claim 1 to a malodor component.

\* \* \* \* \*

UNITED STATES PATENT AND TRADEMARK OFFICE
CERTIFICATE OF CORRECTION

PATENT NO. : 10,137,065 B2
APPLICATION NO. : 15/567727
DATED : November 27, 2018
INVENTOR(S) : Thomas Odén Page 1 of 1

It is certified that error appears in the above-identified patent and that said Letters Patent is hereby corrected as shown below:

On the Title Page

"(22) PCT Filed: Mar. 20, 2016" should be --(22) PCT Filed: Mar. 22, 2016--.

In the Claims

Column 6, Line 27 at Claim 2, "to4.8" should be --to 4.8--.

Signed and Sealed this
Twenty-ninth Day of January, 2019

Andrei Iancu
*Director of the United States Patent and Trademark Office*